US007772272B2

(12) United States Patent
Takagi et al.

(10) Patent No.: US 7,772,272 B2
(45) Date of Patent: *Aug. 10, 2010

(54) METHOD FOR ENHANCING GLUCOSE UPTAKE INTO WARM-BLOODED ANIMAL ADIPOCYTES

(75) Inventors: Toshiyuki Takagi, Shinagawa-ku (JP); Iichiro Shimomura, Toyonaka (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/554,974

(22) PCT Filed: Apr. 27, 2004

(86) PCT No.: PCT/JP2004/006093

§ 371 (c)(1), (2), (4) Date: Mar. 2, 2006

(87) PCT Pub. No.: WO2004/096276

PCT Pub. Date: Nov. 11, 2004

(65) Prior Publication Data

US 2006/0247299 A1  Nov. 2, 2006

(30) Foreign Application Priority Data

Apr. 28, 2003 (JP) ............................ 2003-123781
Jan. 20, 2004 (JP) ............................ 2004-012257

(51) Int. Cl.
*A61K 31/40* (2006.01)
*A61K 38/28* (2006.01)

(52) U.S. Cl. .......................................... 514/423; 514/3
(58) Field of Classification Search ................ 514/423, 514/3
See application file for complete search history.

(56) References Cited

U.S. PATENT DOCUMENTS

| 4,231,938 | A | | 11/1980 | Monaghan et al. |
| 4,346,227 | A | | 8/1982 | Terahara et al. |
| 4,444,784 | A | | 4/1984 | Hoffman et al. |
| 4,739,073 | A | | 4/1988 | Kathawala |
| 5,006,530 | A | | 4/1991 | Angerbauer et al. |
| 5,130,333 | A | | 7/1992 | Pan |
| 5,260,440 | A | | 11/1993 | Hirai et al. |
| 5,273,995 | A | | 12/1993 | Roth |
| 5,298,497 | A | | 3/1994 | Tschollar |
| 5,643,868 | A | * | 7/1997 | Weiner et al. ............. 514/3 |
| 5,798,375 | A | | 8/1998 | Tsujita |
| 5,854,259 | A | | 12/1998 | Fujikawa et al. |
| 5,856,336 | A | | 1/1999 | Fujikawa et al. |
| 6,130,214 | A | | 10/2000 | Lohray |
| 6,159,997 | A | | 12/2000 | Tsujita |
| 6,384,062 | B1 | | 5/2002 | Ikeda et al. |
| 6,414,126 | B1 | | 7/2002 | Ellsworth |

FOREIGN PATENT DOCUMENTS

| EP | 0 671 170 A1 | 9/1995 |
| EP | 0956867 A1 | 11/1999 |
| EP | 1275388 A1 | 1/2003 |
| EP | 1325745 A1 | 7/2003 |
| JP | 04-282324 A | 10/1992 |
| JP | 9071540 A | 3/1997 |
| JP | 2001-294526 A | 10/2001 |
| WO | 95/13063 A1 | 5/1995 |
| WO | 00/45818 A1 | 8/2000 |
| WO | WO 00/45818 A1 | 8/2000 |
| WO | 00/56403 A1 | 9/2000 |
| WO | WO 01/76573 A2 | 10/2001 |
| WO | WO 02/30425 A1 | 4/2002 |
| WO | 2004/052368 A1 | 6/2004 |

OTHER PUBLICATIONS

Paolisso et al., "Simvastatin reduces plasma lipid levels and improves insulin action in elderly, non-insulin dependent diabetes", European Journal of Clinical Pharmacology, vol. 40, No. 1, pp. 27-31.*
Http://www.drugdigest.org/DD/Comparison/NewComparison/0,10621,37-15,00.html (2007).*
Chaudhuri, A., "Vascular Reactivity in Diabetes Mellitus," *Current Diabetes Reports* 2:305-310, 2002.
Cingözbay, B.Y., et al., "Effects of Fluvastatin Treatment on Insulin Sensitivity in Patients With Hyperlipidaemia," *Journal of International Medical Research* 30(1):21-25, Jan.-Feb. 2002.
Dumont, A.S., et al., "Improvement of Endothelial Function in Insulin-Resistant Carotid Arteries Treated With Pravastatin," *Journal of Neurosurgery* 95(3):466-471, Sep. 2001.
Freeman, D.J., et al., "Pravastatin and the Development of Diabetes Mellitus," *Circulation* 103:357-372, Jan. 2001.
Giannoukakis, N., and P.D. Robbins, "Gene and Cell Therapies for Diabetes Mellitus," *Biodrugs* 16(3):149-173, 2002.
Homko, C.J., et al., "Effects of Free Fatty Acids on Glucose Uptake and Utilization in Healthy Women," *Diabetes* 52:487-491, Feb. 2003.
Komai, T., "Effect of Statins on Glucose Metabolism," *Bio Clinica* 17(10):68-73, 2002.
MacMahon, S., et al., "Effects of Lowering Average or Below-Average Cholesterol Levels on the Progression of Carotid Atherosclerosis," *Circulation* 97:1784-1790, 1998.

(Continued)

*Primary Examiner*—Kevin Weddington
(74) *Attorney, Agent, or Firm*—Christensen O'Connor Johnson Kindness PLLC

(57) ABSTRACT

The present invention provides a pharmaceutical composition for enhancement of glucose uptake into warm-blooded animal cells, treatment of diabetes, treatment or prevention of diabetes complications etc., treatment or prevention of diabetes or diabetes complications caused by insulin resistance syndrome, and the like, comprising as an active ingredient an HMG-CoA reductase inhibitor.

7 Claims, No Drawings

OTHER PUBLICATIONS

Mangaloglu, L., et al., "Treatment With Atorvastatin Ameliorates Hepatic Very-Low-Density Lipoprotein Overproduction in an Animal Model of Insulin Resistance, the Fructose-Fed Syrian Golden Hamster: Evidence That Reduced Hypertriglyceridemia Is Accompanied by Improved Hepatic Insulin Sensitivity," *Metabolism* 51(4):409-418, Apr. 2002.

McFarlane, S.I., et al., "Clinical Review 145: Pleiotropic Effects of Statins: Lipid Reduction and Beyond," *Journal of Clinical Endocrinology & Metabolism* 87(4):1451-1458, Apr. 2002.

McVeigh, G.E., and J.N. Cohn, "Endothelial Dysfunction and the Metabolic Syndrome," *Current Diabetes Reports* 3:87-92, 2003.

Merrill, G.F., et al., "AICA Riboside Increased AMP-Activated Protein Kinase, Fatty Acid Oxidation, and Glucose Uptake in Rat Muscle," *American Physiological Society*:E1107-E1112, 1997.

Paolisso, G., et al., "Effects of Simvastatin and Atorvastatin Administration on Insulin Resistance and Respiratory Quotient in Aged Dyslipidemic Non-Insulin Dependent Diabetic Patients," *Atherosclerosis* 150:121-127, 2000.

Shepherd, J., et al., "Pravastatin in Elderly Individuals at Risk of Vascular Disease (PROSPER): A Randomised Controlled Trial," *Lancet* 360:1623-1630, Nov. 23, 2002.

Sorisky, A., "Molecular Links Between Obesity and Cardiovascular Disease," *American Journal of Therapeutics* 9:516-521, 2002.

Sowers, J.R., "Effects of Statins on the Vasculature: Implications for Aggressive Lipid Management in the Cardiovascular Metabolic Syndrome," *American Journal of Cardiology* 91(4A):14B-22B, Feb. 20, 2003.

Usui, H., et al., "HMG-CoA Reductase Inhibitor Ameliorates Diabetic Nephropathy by Its Pleiotropic Effects in Rats," *Nephrology Dialysis Transplantation* 18(2):265-272, Feb. 2003.

Váquez, M., et al., "Experimental Approached to Study PPARγ Agonists as Antidiabetic Drugs," *Methods and Findings in Experimental and Clinical Pharmacology* 24(8):515-523, 2002.

Zhang, B.; et al., "Discovery of a Small Molecule Insulin Mimetic With Antidiabetic Activity in Mice," *Science* 284:974-977, May 7, 1999.

Bellosta, S., et al., "Pleiotropic Effects of Statins in Atherosclerosis and Diabetes," Diabetes Care 23(2):B72-B78, Apr. 2000.

Schulze, M.B., et al., "Adiponectin and Future Coronary Heart Disease Events Among Men With Type 2 Diabetes," Diabetes 54:534-539, Feb. 2005.

Usui, H., et al., HMG-CoA Reduces Inhibitor Ameliorates Diabetic Nephropathy By Its Pleiotropic Effects in Rats, Nephrology Dialysis Transplantation 18:265-272, 2003.

Arita, Y., et al., "Adipocyte-Derived Plasma Protein Adiponectin Acts as a Platelet-Derived Growth Factor-BB-Binding Protein and Regulates Growth Factor-Induced Common Postreceptor Signal in Vascular Smooth Muscle Cell," Circulation 105:2893-2898, Jun. 2002.

Arita, Y., et al., "Paradoxical Decrease of an Adipocyte-Specific Protein, Adiponectin, in Obesity," Biochemical and Biophysical Research Communications 257(1):79-83, Apr. 1999.

Ballantyne, C.M., et al., "Efficacy of Rosuvastatin 10 mg in Patients With the Metabolic Syndrome," American Journal of Cardiology 91(5A):25C-27C, Mar. 2003.

Berg, A.H., et al., "The Adipocyte-Secreted Protein Acrp30 Enhances Hepatic Insulin Action," Nature Medicine 7(8):947-953, Aug. 2001.

Combs, T.P., et al., "Endogenous Glucose Production Is Inhibited by the Adipose-Derived Protein Acrp30," Journal of Clinical Investigation 108(12):1875-1881, Dec. 2001.

Deedwania, P., and D. Hunninghake, "Comparative Effects of Statins on Atherogenic Dyslipidemia in Patients With the Metabolic Syndrome," Journal of the American College of Cardiology 43(5, Suppl A):485A, Mar. 2004 (presented at the 53rd Annual Scientific Session of the American College of Cardiology, New Orleans, Mar. 7-10, 2004) (Abstract 820-1).

Drossos, T., et al., "Results of Pravastatin on Metabolic Parameters of Patients With Diabetes Mellitus Type II Under Simultaneous Treatment With Glybenclamide," Atherosclerosis 144:205, May 1999 (Abstract).

Hotta, K., et al., "Circulating Concentrations of the Adipocyte Protein Adiponectin Are Decreased in Parallel With Reduced Insulin Sensitivity During the Progression to Type 2 Diabetes in Rhesus Monkeys," Diabetes 50(5):1126-1133, May 2001.

Hunninghake, D.B., et al., "Comparative Effects of Simvastatin and Atorvastatin in Hypercholesterolemic Patients With Characteristics of Metabolic Syndrome," Clinical Therapeutics 25(6):1670-1686, Jun. 2003.

Inoue, Y., et al., "A Multi-Centre Study of the Efficacy and Safety of Pravastatin in Hypercholesterolaemic Patients With Non-Insulin-Dependent Diabetes Mellitus," Current Medical Research and Opinion 13(4):187-194, 1994.

Kadowaki, T., and T. Yamauchi, "Adiponectin and Adiponectin Receptors," Endocrine Reviews 26(3):439-451, May 2005.

Kondo, H., et al., "Association of Adiponectin Mutation With Type 2 Diabetes: A Candidate Gene for the Insulin Resistance Syndrome," Diabetes 51(7):2325-2328, Jul. 2002.

Lindsay, R.S., et al., "Adiponectin and Development of Type 2 Diabetes in the Pima Indian Population," Lancet 360(9326):57-58, Jul. 2002.

Maeda, K., et al., "cDNA Cloning and Expression of a Novel Adipose Specific Collagen-Like Factor, apM1 (Adipose Most Abundant Gene Transcript 1)," Biochemical Research Communications 221(2):286-289, 1996.

Maeda, N., "PPARγ Ligands Increase Expression and Plasma Concentrations of Adiponectin, an Adipose-Derived Protein," Diabetes 50(9):2094-2099, Sep. 2001.

Newman, C., et al., "Efficacy of Atorvastatin in Dyslipidemic Patients With Metabolic Syndrome in the Access Study," Diabetes 52(Suppl 1):A494, 2003 (presented at the 63rd Scientific Sessions of the American Diabetes Association, New Orleans, Jun. 13-17, 2003) (Abstract 2141-PO).

Okamoto, Y., et al., "Adiponectin Reduces Atherosclerosis in Apolipoprotein E-Deficient Mice," Circulation 106(22):2767-2770, Nov. 2002.

Olsson, A.G., et al., "Rosuvastatin: A Highly Effective New HMG-CoA Reductase Inhibitor," Cardiovascular Drug Reviews 20(4):303-328, Jan. 2002.

Orsi, A., et al., "Simvastatin-Associated Memory Loss," Pharmacotherapy 21(6):767-769, Jun. 2001.

Ouchi, N., et al., "Adipocyte-Derived Plasma Protein, Adiponectin, Suppresses Lipid Accumulation and Class A Scavenger Receptor Expression in Human Monocyte-Derived Macrophages," Circulation 103(8):1057-1063, Feb. 2001.

Ouchi N., et al., "Adiponectin, an Adipocyte-Derived Plasma Protein, Inhibits Endothelial NF-κB Signaling Through a cAMP-Dependent Pathway," Circulation 102(11):1296-1301, Sep. 2000.

Ouchi, N., "Novel Modulator for Endothelial Adhesion Molecules: Adipocyte-Derived Plasma Protein Adiponectin," Circulation 100(25):2473-2476, Dec. 1999.

Paniagua, J.A., et al., "Cerivastatin Improves Insulin Sensitivity and Insulin Secretion in Early-State Obese Type 2 Diabetes," Diabetes 51(8):2596-2603, Aug. 2002.

Reaven, G.M., "Banting Lecture 1988: Role of Insulin Resistance in Human Disease," Diabetes 37(12):1595-1607, Dec. 1988.

Ross, R., "The Pathogenesis of Atherosclerosis: A Perspective for the 1990s," Nature 362(6423):801-809, Apr. 1993.

Saito, Y., et al., "Statin Reverses Reduction of Adiponectin Receptor Expression in Infarcted Heart and in TNF-α-Treated Cardiomyocytes in Association With Improved Glucose Uptake," American Journal of Physiological: Heart and Circulatory Physiology 293(6):H3490-H3497, Dec. 2007.

Schulze, M.B., et al., "Adiponectin and Future Coronary Heart Disease Events Among Men With Type 2 Diabetes," Diabetes 54(2):534-539, Feb. 2005.

Sugimoto, T., "Pravastatin Versus Simvastatin in Hyperlipidemic Patients With Type 2 Diabetes Mellitus," Current Therapeutic Research 60(7):404-413, Jul. 1999.

Weyer, C., et al., "Hypoadiponectinemia in Obesity and Type 2 Diabetes: Close Association With Insulin Resistance and Hyperinsulinemia, "Journal of Clinical Endocrinology & Metabolism 86(5):1930-1935, May 2001.

Yamauchi, T., et al., "The Fat-Derived Hormone Adiponectin Reverses Insulin Resistance Associated With Both Lipoatrophy and Obesity," Nature Medicine 7(8):941-946, Aug. 2001.

Yokota, T., et al., "Adiponectin, a New Member of the Family of Soluble Defense Collagesns, Negatively Regulates the Growth of Myelomonocytic Progenitors and the Functions of Macrophages," Blood 96(5):1723-1732, Sep. 2000.

Zoccali, C., et al., "Adiponectin, Metabolic Risk Factors, and Cardiovascular Events Among Patients With End-Stage Renal Disease," Journal of the American Society of Nephrology 13(1):134-141, Jan. 2002.

Supplementary European Search Report dated Jul. 14, 2009, issued in corresponding European Application No. EP 04 72 9730, filed Apr. 27, 2004.

* cited by examiner

_US 7,772,272 B2_

METHOD FOR ENHANCING GLUCOSE UPTAKE INTO WARM-BLOODED ANIMAL ADIPOCYTES

TECHNICAL FIELD

The present invention relates to a pharmaceutical composition containing as an active ingredient one or more HMG-CoA reductase inhibitor(s) for enhancement of glucose uptake into warm-blooded animal cells; enhancement of glucose uptake into warm-blooded animal cells in the presence of insulin; treatment of diabetes, hyperglycemia, glucose intolerance or gestational diabetes mellitus; treatment or prevention of diabetes complications (including retinopathy, nephropathy, neuropathy, cataract and coronary artery disease); or treatment or prevention of diabetes, hyperglycemia, glucose intolerance, gestational diabetes mellitus or diabetes complications (including retinopathy, nephropathy, neuropathy, cataract and coronary artery disease) caused by insulin resistance syndrome, and, a method comprising administration of an effective amount of one or more HMG-CoA reductase inhibitor(s) to a warm-blooded animal for enhancement of glucose uptake into warm-blooded animal cells; enhancement of glucose uptake into warm-blooded animal cells in the presence of insulin; treatment of diabetes, hyperglycemia, glucose intolerance or gestational diabetes mellitus; treatment or prevention of diabetes complications (including retinopathy, nephropathy, neuropathy, cataract and coronary artery disease); or treatment or prevention of diabetes, hyperglycemia, glucose intolerance, gestational diabetes mellitus or diabetes complications (including retinopathy, nephropathy, neuropathy, cataract and coronary artery disease) caused by insulin resistance syndrome.

BACKGROUND ART

Blood glucose level is primarily determined by the balance between the uptake of glucose in peripheral tissues such as muscle and fat and the production of glucose in the liver. Insulin, which is secreted from the pancreas according to the blood glucose level, maintains homeostasis of blood glucose levels by promoting glucose uptake in these peripheral tissues and suppressing glucose production in the liver. When diabetes and so forth occurs caused by increased insulin resistance, the action of insulin weakens resulting in a disorder in the blood glucose level control function. As a result, a state of elevated blood glucose continues resulting in glucotoxicity throughout the body, and severe hyperglycemia causes diabetes complications such as retinopathy and neuropathy. Medicaments that enhance glucose uptake in peripheral tissues have the action of improving hyperglycemia by promoting glucose metabolism, and are useful for the treatment or prevention of diabetes, hyperglycemia, glucose intolerance, gestational diabetes mellitus or diabetes complications (Homko, C. J. et al., Diabetes, 2003, 52, 487-491; Giannoukakis, N. et al., Biodrugs, 2002, 16, 149-173).

A disease state associated with increased insulin resistance, or so-called insulin resistance syndrome, is the major cause of diabetes, while also being considered to be the fundamental cause of lifestyle diseases including circulatory diseases (arteriosclerosis, hypertension, etc.) and obesity (McVeigh, G. E. et al., Current Diabetes Reports, 2003, 3, 87-92; Chaudhuri, A. et al., Current Diabetes Reports, 2002, 2, 305-310; Sorisky, A. et al., American Journal of Therapeutics, 2002, 9, 516-521). Insulin resistance is related to glucose uptake in peripheral tissues, and improvement of insulin resistance is known to promote glucose uptake in peripheral tissues (Vazquez, M. et al., Methods & Findings in Experimental & Clinical Pharmacology, 2002, 24, 513-523). Thus, medicaments that enhance glucose uptake in peripheral tissues by acting on the function of insulin to improve insulin resistance are useful for the treatment or prevention of diabetes, hyperglycemia, glucose intolerance, gestational diabetes mellitus or diabetes complications caused by insulin resistance syndrome.

Although certain types of quinone compounds or nucleic acid derivatives have been known to demonstrate glucose uptake enhancing action in cells of peripheral tissues (for example, Zhang, B. et al., Science, 1999, 284, 974-977; Merill, G. F. et al., American Journal of Physiology, Endocrinology and Metabolism, 1997, 273, E1107-E1112, and so forth), HMG-CoA reductase inhibitors have not been known to demonstrate glucose uptake enhancing action on warm-blooded animal cells.

HMG-CoA (3-hydroxy-3-methylglutaryl-CoA) reductase inhibitors are well-known hyperlipemia therapeutic medicaments (for example, U.S. Pat. No. 4,346,227 et al.). Statins are typical HMG-CoA reductase inhibitors, and disease preventive effects in humans have been confirmed in various clinical studies. For example, pravastatin has been reported to demonstrate effects (preventive effects) that suppress the onset of arteriosclerosis, coronary artery disease and diabetes in a clinical study targeted at hyperlipemia patients (for example, MacMahon, S. et al., Circulation, 1998, 97, 1784-1790; Shepherd, J. et al., Lancet, 2002, 360, 1623-1630; Freeman, D. J. et al., Circulation, 2001, 103, 357-362; etc.).

However, HMG-CoA reductase inhibitors are not known to demonstrate therapeutic effects for diabetes, hyperglycemia, glucose intolerance or gestational diabetes mellitus as well as therapeutic or preventive effects for diabetes complications.

DISCLOSURE OF THE INVENTION

The inventors of the present invention found that an HMG-CoA reductase inhibitor has superior glucose uptake enhancing action on warm-blooded animal cells, and is useful as a pharmaceutical composition for enhancement of glucose uptake into warm-blooded animal cells; enhancement of glucose uptake into warm-blooded animal cells in the presence of insulin; treatment of diabetes, hyperglycemia, glucose intolerance or gestational diabetes mellitus; treatment or prevention of diabetes complications (including retinopathy, nephropathy, neuropathy, cataract and coronary artery disease); or treatment or prevention of diabetes, hyperglycemia, glucose intolerance, gestational diabetes mellitus or diabetes complications (including retinopathy, nephropathy, neuropathy, cataract and coronary artery disease) caused by insulin resistance syndrome, thereby leading to completion of the present invention.

The present invention provides a pharmaceutical composition comprising as an active ingredient one or more HMG-CoA reductase inhibitor(s) for enhancement of glucose uptake into warm-blooded animal cells; enhancement of glucose uptake into warm-blooded animal cells in the presence of insulin; treatment of diabetes, hyperglycemia, glucose intolerance or gestational diabetes mellitus; treatment or prevention of diabetes complications (including retinopathy, nephropathy, neuropathy, cataract and coronary artery disease); or treatment or prevention of diabetes, hyperglycemia, glucose intolerance, gestational diabetes mellitus or diabetes complications (including retinopathy, nephropathy, neuropathy, cataract and coronary artery disease) caused by insulin resistance syndrome, and, a method comprising administration of an effective amount of one or more HMG-CoA reductase inhibitor(s) to a warm-blooded animal for enhancement of glucose uptake into warm-blooded animal cells; enhancement of glucose uptake into warm-blooded animal cells in the presence of insulin; treatment of diabetes, hyperglycemia, glucose intolerance or gestational diabetes mellitus; treatment or prevention of diabetes complications (including retinopathy, nephropathy, neuropathy, cataract and coronary artery disease); or treatment or prevention of diabetes, hyperglycemia, glucose intolerance, gestational diabetes mellitus or diabetes complications (including retinopathy, nephropathy, neuropathy, cataract and coronary artery disease) caused by insulin resistance syndrome.

The present invention is:

(1) a pharmaceutical composition for enhancement of glucose uptake into warm-blooded animal cells comprising as an active ingredient one or more HMG-CoA reductase inhibitor(s);

(2) a pharmaceutical composition for enhancement of glucose uptake into warm-blooded animals cells in the presence of insulin comprising as an active ingredient one or more HMG-CoA reductase inhibitor(s);

(3) a pharmaceutical composition as (1) or (2), wherein the HMG-CoA reductase inhibitor is selected from the group consisting of pravastatin, lovastatin, simvastatin, fluvastatin, cerivastatin, atorvastatin, pitavastatin and rosuvastatin;

(4) a pharmaceutical composition as (1) or (2), wherein the HMG-CoA reductase inhibitor is a water-soluble HMG-CoA reductase inhibitor;

(5) a pharmaceutical composition as (1) or (2), wherein the HMG-CoA reductase inhibitor is a medicament selected from the group consisting of pravastatin and rosuvastatin;

(6) a pharmaceutical composition as (1) or (2), wherein the HMG-CoA reductase inhibitor is pravastatin;

(7) a pharmaceutical composition for the treatment of diabetes, hyperglycemia, glucose intolerance or gestational diabetes mellitus, or the treatment or prevention of diabetes complications (including retinopathy, nephropathy, neuropathy, cataract and coronary artery disease), comprising as an active ingredient one or more medicament(s) selected from the group consisting of pravastatin, lovastatin, simvastatin, fluvastatin, cerivastatin, atorvastatin, pitavastatin and rosuvastatin;

(8) a pharmaceutical composition for the treatment of diabetes, hyperglycemia, glucose intolerance or gestational diabetes mellitus caused by insulin resistance syndrome, or the treatment or prevention of diabetes complications (including retinopathy, nephropathy, neuropathy, cataract and coronary artery disease) caused by insulin resistance syndrome, comprising as an active ingredient one or more medicament(s) selected from the group consisting of pravastatin, lovastatin, simvastatin, fluvastatin, cerivastatin, atorvastatin, pitavastatin and rosuvastatin;

(9) a pharmaceutical composition for the treatment of diabetes, hyperglycemia, glucose intolerance or gestational diabetes mellitus, or the treatment or prevention of diabetes complications (including retinopathy, nephropathy, neuropathy, cataract and coronary artery disease), comprising as an active ingredient one or more water-soluble HMG-CoA reductase inhibitor(s);

(10) a pharmaceutical composition for the treatment of diabetes, hyperglycemia, glucose intolerance or gestational diabetes mellitus caused by insulin resistance syndrome, or the treatment or prevention of diabetes complications (including retinopathy, nephropathy, neuropathy, cataract and coronary artery disease) caused by insulin resistance syndrome, comprising as an active ingredient one or more water-soluble HMG-CoA reductase inhibitor(s);

(11) a pharmaceutical composition as (9) or (10), wherein the water-soluble HMG-CoA reductase inhibitor is selected from the group consisting of pravastatin and rosuvastatin;

(12) a pharmaceutical composition as (9) or (10), wherein the water-soluble HMG-CoA reductase inhibitor is pravastatin;

(13) a method for enhancing glucose uptake into warm-blooded animal cells comprising administration of an effective amount of one or more HMG-CoA reductase inhibitor(s) to a warm-blooded animal;

(14) a method for enhancing glucose uptake into warm-blooded animal cells in the presence of insulin comprising administration of an effective amount of one or more HMG-CoA reductase inhibitor(s) to a warm-blooded animal;

(15) a method as (13) or (14), wherein the HMG-CoA reductase inhibitor is selected from the group consisting of pravastatin, lovastatin, simvastatin, fluvastatin, cerivastatin, atorvastatin, pitavastatin and rosuvastatin;

(16) a method as (13) or (14), wherein the HMG-CoA reductase inhibitor is a water-soluble HMG-CoA reductase inhibitor;

(17) a method as (13) or (14), wherein the HMG-CoA reductase inhibitor is selected from the group consisting of pravastatin and rosuvastatin;

(18) a method as (13) or (14), wherein the HMG-CoA reductase inhibitor is pravastatin;

(19) a method for the treatment of diabetes, hyperglycemia, glucose intolerance or gestational diabetes mellitus, or the treatment or prevention of diabetes complications (including retinopathy, nephropathy, neuropathy, cataract and coronary artery disease), comprising administration of an effective amount of one or more medicament(s) selected from the group consisting of pravastatin, lovastatin, simvastatin, fluvastatin, cerivastatin, atorvastatin, pitavastatin and rosuvastatin to a warm-blooded animal;

(20) a method for the treatment of diabetes, hyperglycemia, glucose intolerance or gestational diabetes mellitus caused by insulin resistance syndrome, or the treatment or prevention of diabetes complications (including retinopathy, nephropathy, neuropathy, cataract and coronary artery disease) caused by insulin resistance syndrome, comprising administration of an effective amount of one or more medicament(s) selected from the group consisting of pravastatin, lovastatin, simvastatin, fluvastatin, cerivastatin, atorvastatin, pitavastatin and rosuvastatin to a warm-blooded animal;

(21) a method for the treatment of diabetes, hyperglycemia, glucose intolerance or gestational diabetes mellitus, or the treatment or prevention of diabetes complications (including retinopathy, nephropathy, neuropathy, cataract and coronary artery disease), comprising administration of an effective amount of one or more water-soluble HMG-CoA reductase inhibitor(s) to a warm-blooded animal;

(22) a method for the treatment of diabetes, hyperglycemia, glucose intolerance or gestational diabetes mellitus caused by insulin resistance syndrome, or the treatment or prevention of diabetes complications (including retinopathy, nephropathy, neuropathy, cataract and coronary artery disease) caused by insulin resistance syndrome, comprising administration of an effective amount of one or more water-soluble HMG-CoA reductase inhibitor(s) to a warm-blooded animal;

(23) a method as (21) or (22), wherein the water-soluble HMG-CoA reductase inhibitor is selected from the group consisting of pravastatin and rosuvastatin;

(24) a method as (21) or (22), wherein the water-soluble HMG-CoA reductase inhibitor is pravastatin; or

(25) a method as any one of (13) to (24), wherein the warm-blooded animal is a human.

There are no particular restrictions on the HMG-CoA reductase inhibitor(s) serving as an active ingredient compound of the present invention provided it is a compound that demonstrates HMG-CoA reductase inhibitory action, examples of which include compounds having HMG-CoA reductase inhibitory action, pharmacologically acceptable salts thereof, or pharmacologically acceptable esters thereof as described in Japanese Patent Application (Kokai) No. Sho 57-2240 (U.S. Pat. No. 4,346,227), Japanese Patent Application (Kokai) No. Sho 57-163374 (U.S. Pat. No. 4,231,938), Japanese Patent Application (Kokai) No. Sho 56-122375 (U.S. Pat. No. 4,444,784), Japanese Patent Application (Kokai) No. Sho 60-500015 (U.S. Pat. No. 4,739,073), Japanese Patent Application (Kokai) No. Hei 1-216974 (U.S. Pat. No. 5,006,530), Japanese Patent Application (Kokai) No. Hei 3-58967 (U.S. Pat. No. 5,273,995), Japanese Patent Application (Kokai) No. Hei 1-279866 (U.S. Pat. Nos. 5,854,259 and 5,856,336) or Japanese Patent Application (Kokai) No. Hei 5-178841 (U.S. Pat. No. 5,260,440), preferably pravastatin, lovastatin, simvastatin, fluvastatin, cerivastatin, atorvastatin, pitavastatin or rosuvastatin, more preferably pravastatin or rosuvastatin, and most preferably pravastatin.

For an HMG-CoA reductase inhibitor serving as an active ingredient compound of the present invention, a water-soluble HMG-CoA reductase inhibitor such as pravastatin and rosuvastatin is preferable. In the present invention, a water-soluble HMG-CoA reductase inhibitor is an HMG-CoA reductase inhibitor in which the logarithm of the partition coefficient measured between phosphate buffer solution (pH 7.0 to 8.0, preferably pH 7.0 to 7.5, and more preferably pH 7.0) and 1-octanol [log(test substance concentration in 1-octanol phase/test substance concentration in buffer solution phase)] is 1.0 or less (preferably 0.5 or less, and more preferably 0.0 or less) (McTaggart, F. et al., The American Journal of Cardiology, 2001, 87, 28B-32B; Chapman, M. J. et al., Atherosclerosis Supplements, 2002, 33-37; Shimada, Y. et al., Progress in Medicine, 1998, 18, 957-962). The aforementioned partition coefficient can be measured according to ordinary methods (Partition Coefficient (n-octanol/water), OECD Guidelines for Testing of Chemicals, Section 1, Physical Chemical Properties, Paris, 1981, 107; Shimada, Y. et al., Progress in Medicine, 1998, 18, 957-962) or similar methods thereto.

In addition, for an HMG-CoA reductase inhibitor serving as an active ingredient compound of the present invention, pravastatin or derivative thereof, or rosuvastatin or derivative thereof, is preferable. In the present invention, a derivative of pravastatin is a compound having HMG-CoA reductase inhibitory action, a pharmacologically acceptable salt thereof or ester thereof as described in Japanese Patent Application (Kokai) No. Sho 57-2240 (U.S. Pat. No. 4,346,227), while a derivative of rosuvastatin is a compound having HMG-CoA reductase inhibitory action, a pharmacologically acceptable salt thereof or ester thereof as described in Japanese Patent Application (Kokai) No. Hei 5-178841 (U.S. Pat. No. 5,260,440).

Pravastatin is (+)-(3R,5R)-3,5-dihydroxy-7-[(1S,2S,6S,8S,8aR)-6-hydroxy-2-methyl-8-[(S)-2-methylbutyryloxy]-1,2,6,7,8,8a-hexahydro-1-naphthyl]heptanoic acid, and includes its pharmacologically acceptable salts or esters (for example, monosodium salt of the aforementioned pravastatin, etc.) as described in Japanese Patent Application (Kokai) No. Sho 57-2240 (U.S. Pat. No. 4,346,227). Lovastatin is (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl (S)-2-methylbutyrate, and includes its pharmacologically acceptable salts or esters as described in Japanese Patent Application (Kokai) No. Sho 57-163374 (U.S. Pat. No. 4,231,938). Simvastatin is (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl 2,2-dimethylbutyrate, and includes its pharmacologically acceptable salts or esters as described in Japanese Patent Application (Kokai) No. Sho 56-122375 (U.S. Pat. No. 4,444,784). Fluvastatin is (±)-(3R*,5S*,6E)-7-[3-(4-fluorophenyl)-1-(1-methylethyl)-1H-indol-2-yl]-3,5-dihydroxy-6-heptenoic acid, and includes its pharmacologically acceptable salts or esters (for example, monosodium salt of the aforementioned fluvastatin, etc.) as described in Japanese Patent Application (Kokai) No. Sho 60-500015 (U.S. Pat. No. 4,739,073). Cerivastatin is (3R,5S,6E)-7-[4-(4-fluorophenyl)-2,6-di-(1-methylethyl)-5-methoxymethylpyridin-3-yl]-3,5-dihydroxy-6-heptenoic acid, and includes its pharmacologically acceptable salts or esters (for example, monosodium salt of the aforementioned cerivastatin, etc.) as described in Japanese Patent Application (Kokai) No. Hei 1-216974 (U.S. Pat. No. 5,006,530). Atorvastatin is (3R,5S)-7-[2-(4-fluorophenyl)-5-(1-methylethyl)-3-phenyl-4-phenylaminocarbonyl-1H-pyrrol-1-yl]-3,5-dihydroxyheptanoic acid, and includes its pharmacologically acceptable salts or esters (for example, ½ calcium salt of the aforementioned atorvastatin, etc.) as described in Japanese Patent Application (Kokai) No. Hei 3-58967 (U.S. Pat. No. 5,273,995). Pitavastatin is (E)-3,5-dihydroxy-7-[4'-(4"-fluorophenyl)-2'-cyclopropylquinolin-3'-yl]-6-heptenoic acid, and includes its pharmacologically acceptable salts or esters (for example, ½ calcium salt of the aforementioned pitavastatin, etc.) as described in Japanese Patent Application (Kokai) No. Hei 1-279866 (U.S. Pat. Nos. 5,854,259 and 5,856,336). Rosuvastatin is (+)-(3R,5S)-7-[4-(4-fluorophenyl)-6-isopropyl-2-(N-methyl-N-methanesulfonylamino)pyrimidin-5-yl]-3,5-dihydroxy-6(E)-heptenoic acid, and includes its pharmacologically acceptable salts or esters (for example, ½ calcium salt of the aforementioned rosuvastatin, etc.) as described in Japanese Patent Application (Kokai) No. Hei 5-178841 (U.S. Pat. No. 5,260,440).

The following indicates the two-dimensional structural formulas of major HMG-CoA reductase inhibitors.

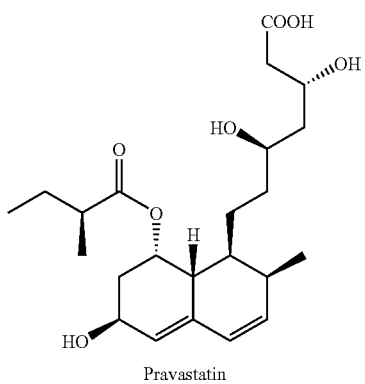

Pravastatin

-continued

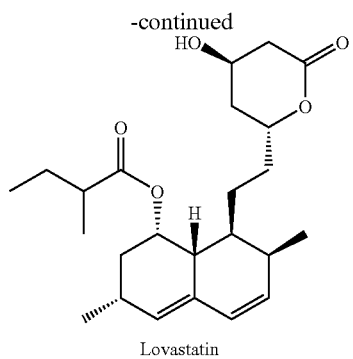
Lovastatin

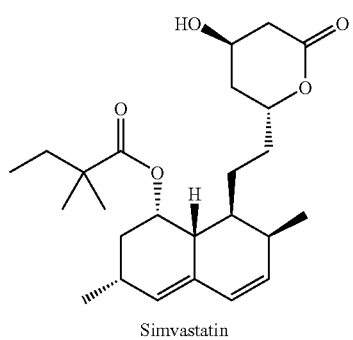
Simvastatin

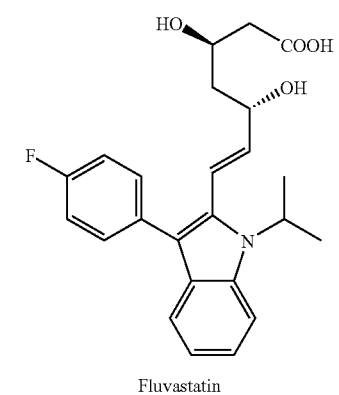
Fluvastatin

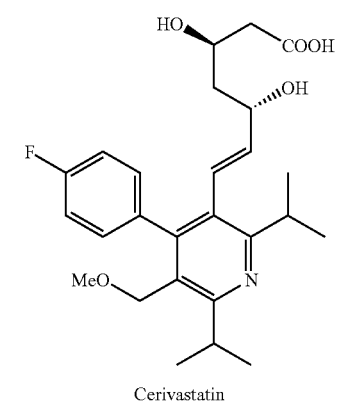
Cerivastatin

-continued

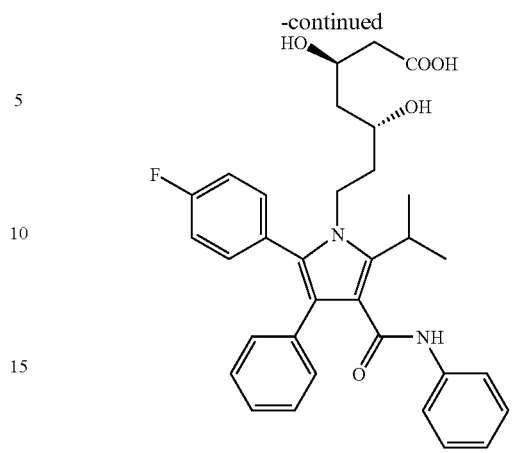
Atorvastatin

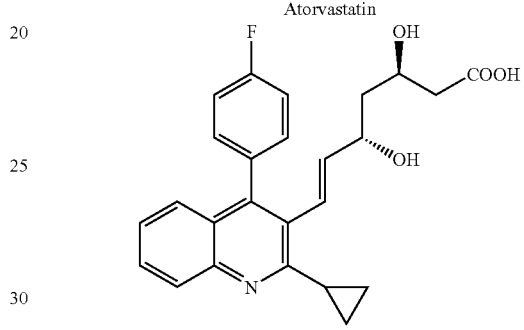
Pitavastatin

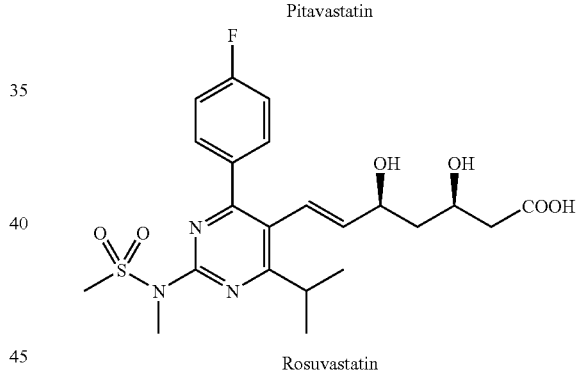
Rosuvastatin

In the case where the aforementioned HMG-CoA reductase inhibitor has an asymmetric carbon, all of its racemate, its optical isomers and mixtures thereof are included in the HMG-CoA reductase inhibitor of the present invention. In addition, hydrates of the aforementioned HMG-CoA reductase inhibitors are also included in the HMG-CoA reductase inhibitor of the present invention.

For an HMG-CoA reductase inhibitor serving as an active ingredient compound in the present invention, one type of compound can be used alone, or a mixture of two or more types of compounds can be used. In the case of using a mixture of two or more types of compounds, the compounds can be used simultaneously or each of compounds can be used separately at different times.

An HMG-CoA reductase inhibitor serving as an active ingredient of the present invention can easily be prepared in accordance with known methods [for example, Japanese Patent Application (Kokai) No. Sho 57-2240 (U.S. Pat. No. 4,346,227), Japanese Patent Application (Kokai) No. Sho 57-163374 (U.S. Pat. No. 4,231,938), Japanese Patent Application (Kokai) No. Sho 56-122375 (U.S. Pat. No. 4,444,784), Japanese Patent Application (Kokai) No. Sho 60-500015 (U.S. Pat. No. 4,739,073), Japanese Patent Application (Kokai) No. Hei 1-216974 (U.S. Pat. No. 5,006,530), Japanese Patent Application (Kokai) No. Hei 3-58967 (U.S. Pat. No. 5,273,995), Japanese Patent Application (Kokai) No. Hei 1-279866 (U.S. Pat. Nos. 5,854,259 and 5,856,336), Japanese Patent Application (Kokai) No. Hei 5-178841 (U.S. Pat. No. 5,260,440), etc.] or similar methods thereto.

INDUSTRIAL APPLICABILITY

In the case of using the HMG-CoA reductase inhibitor(s) serving as an active ingredient of the present invention as a pharmaceutical (pharmaceutical composition for treatment or prevention of the aforementioned diseases), it can be administered in the form of a bulk medicament of the pharmaceutical itself; or it can be orally administered in a formulation such as tablet, capsule, granules, pill, powder, liquid, syrup, troche, suspension, emulsion, etc. or be parenterally administered in a formulation such as an injection, suppository or patch, etc., which formulations are made by mixing the HMG-CoA reductase inhibitor with a suitably pharmacologically acceptable excipient, binder and so forth. An oral administration is preferred.

These formulations are prepared using well-known methods using additives such as excipients, binders, disintegrants, lubricants, emulsifiers, stabilizers, corrigents, diluents, injection solvents and so forth.

An excipient may be, for example, an organic excipient or inorganic excipient. Examples of organic excipients include sugar derivatives such as lactose, sucrose, glucose, mannitol and sorbitol; starch derivatives such as cornstarch, potato starch, alpha starch, dextrin and carboxymethyl starch; cellulose derivatives such as crystalline cellulose, hydroxypropyl cellulose, low substituted hydroxypropyl cellulose, hydroxypropylmethyl cellulose, carboxymethyl cellulose, calcium carboxymethyl cellulose, and internally-crosslinked sodium carboxymethyl cellulose; gum arabic; dextran; and, pullulan. Examples of inorganic excipients include silicic acid salt derivatives such as light anhydrous silicic acid, synthetic aluminium silicate, calcium silicate, and magnesium metasilicate aluminate; phosphoric acid salts such as calcium phosphate; carbonic acid salts such as calcium carbonate; and sulfuric acid salts such as calcium sulfate.

Examples of binders include the compounds as described for the aforementioned excipient; gelatin; polyvinylpyrrolidone; and, polyethylene glycol.

Examples of disintegrants include the compounds as described for the aforementioned excipient; chemically modified starch or cellulose derivatives such as crosscarmelose sodium and sodium carboxymethyl starch; and, crosslinked polyvinylpyrrolidone.

Examples of lubricants include talc; stearic acid; metal stearates such as calcium stearate and magnesium stearate; colloidal silica; waxes such as bee gum and spermaceti; boric acid; glycol; DL-leucine; carboxylic acids such as fumaric acid and adipic acid; carboxylic acid sodium salts such as sodium benzoate; sulfates such as sodium sulfate; lauryl sulfates such as sodium lauryl sulfate and magnesium lauryl sulfate; silicic acids such as anhydrous silicic acid and silicic acid hydrate; and the above starch derivatives as for the aforementioned excipients.

Examples of emulsifiers include colloidal clays such as bentonite and bee gum; metal hydroxides such as magnesium hydroxide and aluminium hydroxide; anionic surfactants such as sodium lauryl sulfate and calcium stearate; cationic surfactants such as benzalkonium chloride; and, nonionic surfactants such as polyoxyethylene alkyl ether, polyoxyethylene sorbitan fatty acid ester, and sucrose fatty acid ester.

Examples of stabilizers include parahydroxybenzoic acid esters such as methyl paraben and propyl paraben; alcohols such as chlorobutanol, benzyl alcohol or phenylethyl alcohol; benzalkonium chloride; phenols such as phenol and cresol; thimerosal; dehydroacetic acid; and sorbic acid.

Examples of corrigents include ordinarily used sweeteners, sour flavourings, fragrances, etc.

Examples of diluents include water, ethanol, propylene glycol, ethoxyisostearyl alcohol and polyoxyethylene sorbitan fatty acid ester.

Examples of injection solvents include water, ethanol and glycerin.

The HMG-CoA reductase inhibitor(s) serving as an active ingredient of the present invention can be administered to a warm-blooded animal (and particularly a human). The dose can be varied depending on various conditions such as the symptoms and age of the patient. In the case of oral administration, 0.1 mg (preferably 0.5 mg) as a lower limit and 1000 mg (preferably 500 mg) as an upper limit can be administered once to six times per day for a human adult depending on the symptoms. In the case of parenteral administration, 0.01 mg (preferably 0.05 mg) as a lower limit and 100 mg (preferably 50 mg) as an upper limit can be administered once to six times per day for a human adult depending on the symptoms.

Since the HMG-CoA reductase inhibitor(s) serving as an active ingredient of the present invention has superior glucose uptake enhancing action in the presence or absence of insulin (preferably in the presence of insulin) in warm-blooded animal cells (preferably warm-blooded animal adipocytes), it is useful as a pharmaceutical composition for enhancement of glucose uptake into warm-blooded animal cells (preferably warm-blooded animal adipocytes); enhancement of glucose uptake into warm-blooded animal cells (preferably warm-blooded animal adipocytes) in the presence of insulin; treatment of diabetes, hyperglycemia, glucose intolerance or gestational diabetes mellitus; treatment or prevention of diabetes complications (including retinopathy, nephropathy, neuropathy, cataract and coronary artery disease); or treatment or prevention of diabetes, hyperglycemia, glucose intolerance, gestational diabetes mellitus or diabetes complications (including retinopathy, nephropathy, neuropathy, cataract and coronary artery disease) caused by insulin resistance syndrome, preferably for enhancement of glucose uptake into warm-blooded animal cells in the presence of insulin; treatment of diabetes; treatment or prevention of diabetes complications (including retinopathy, nephropathy, neuropathy, cataract and coronary artery disease); treatment of diabetes, hyperglycemia, glucose intolerance or gestational diabetes mellitus caused by insulin resistance syndrome; or treatment or prevention of diabetes complications (including retinopathy, nephropathy, neuropathy, cataract and coronary artery disease) caused by insulin resistance syndrome, more preferably for enhancement of glucose uptake into warm-blooded animal cells in the presence of insulin; treatment of diabetes, hyperglycemia, glucose intolerance or gestational diabetes mellitus caused by insulin resistance syndrome; or treatment or prevention of diabetes complications (including retinopathy, nephropathy, neuropathy, cataract and coronary artery disease) caused by insulin resistance syndrome, and even more preferably for enhancement of glucose uptake into warm-blooded animal cells in the presence of insulin; treatment of diabetes caused by insulin resistance syndrome; or treatment or prevention of diabetes complications (including retinopathy, nephropathy, neuropathy, cataract and coronary artery disease) caused by insulin resistance syndrome.

In addition, the aforementioned pharmaceutical composition is preferably for warm-blooded animals, and more preferably for humans. A pharmaceutical composition for treatment or prevention of the present invention is preferably a pharmaceutical composition for treatment.

BEST MODE FOR CARRYING OUT THE INVENTION

Although the following provides a more detailed explanation of the present invention by indicating Examples and Formulation examples, the scope of the present invention is not limited thereto.

EXAMPLE 1

Glucose Uptake Enhancing Action (In Vitro)

(1) Cell Culturing

Preadipocyte cell line 3T3-L1 was purchased from the American Type Culture Collection (ATCC). The 3T3-L1 cells were plated onto a 24-well, collagen-coated plate and cultured to saturation in growth medium (DMEM, 25 mM glucose, 10% FCS, 100 u/ml penicillin, 0.1 mg/ml streptomycin) under conditions of 37° C. and 5% $CO_2$. Five days after cell proliferation had reached a saturated state, the medium was replaced with medium (DMEM, 25 mM glucose, 10% FCS, 100 u/ml penicillin, 0.1 mg/ml streptomycin) to which had been added 1 µM insulin, 0.5 mM 3-isobutyl-1-methylxanthine and 1 µM dexamethazone to initiate adipocyte differentiation. Two days later, the medium was replaced with growth medium containing 1 µM insulin followed by additionally culturing the cells for 2 days. Subsequently, the medium was replaced with fresh growth medium every 3 days, and the 3T3-L1 adipocytes were prepared on day 10 after the start of differentiation.

Test compounds that were poorly soluble in water were used after dissolving in DMSO. Test compounds that were easily soluble in water were dissolved in sterile water followed by addition of the same amount of DMSO as that used for the aforementioned poorly water-soluble test compounds. In addition, in the case of test compounds that are poorly soluble in water, the test compound may be dissolved in ethanol and used following the addition of 0.1 N aqueous sodium hydroxide solution after shaking as necessary.

After allowing the 3T3-L1 cells to adequately differentiate into adipocytes, a test compound was added to the medium to a final concentration of 10 µM followed by culturing the cells for 72 hours.

(2) Measurement of Glucose Uptake

Following treatment with the test compound, the cells were washed with KRBH buffer solution (6.91 g/l NaCl, 0.37 g/l KCl, 0.30 g/l $MgSO_4 \cdot 7H_2O$, 0.19 g/l $CaCl_2 \cdot 2H_2O$, 0.21 g/l $K_2HPO_4$, 25 mM HEPES, 2 g/l $NaHCO_3$, 0.1% BSA (Sigma), 0.11 g/l sodium pyruvate, 100 u/ml penicillin, 0.1 mg/ml streptomycin) and then cultured for 3.5 hours at 37° C. Subsequently, insulin was added to the cells followed by additionally culturing the cells for 30 minutes.

Measurement of glucose uptake was carried out in the manner described below. Namely, 0.1 µCi of $^3$H-labeled 2-deoxyglucose was added to the medium followed by removal of the medium ten minutes later and washing with phosphate buffer solution (phosphate-buffered saline: PBS, pH 7.4). After washing, 200 µl of 1 N aqueous sodium hydroxide solution were added to the cells to lyse the cells. 160 µl of the cell lysate were mixed with 4 ml of Hionic Fluor (Perkin-Elmer) liquid scintillation counter cocktail followed by measurement of the radioactivity in the cell lysate with a liquid scintillation counter (Packard). The determined radioactivity of the $^3$H-labeled was used as an indicator of the amount of glucose taken up into the cells. The amount of glucose uptake into the cells was 1.9 times higher (P<0.001) in the group in which pravastatin was used for the test compound than in the control group.

According to this result, an HMG-CoA reductase inhibitor serving as an active ingredient of the present invention was determined to have superior action of enhancing glucose uptake into warm-blooded animal cells, and be useful as a pharmaceutical composition for enhancement of glucose uptake into warm-blooded animal cells; enhancement of glucose uptake into warm-blooded animal cells in the presence of insulin; treatment of diabetes; treatment or prevention of diabetes complications (including retinopathy, nephropathy, neuropathy, cataract and coronary artery disease); treatment or prevention of diabetes, hyperglycemia, glucose intolerance, gestational diabetes mellitus or diabetes complications (including retinopathy, nephropathy, neuropathy, cataract and coronary artery disease) caused by insulin resistance syndrome; etc.

EXAMPLE 2

Glucose Uptake Enhancing Action (In Vivo)

(1) Administration of Pravastatin to Mice in Feed (i) Test Animals

C57BL/ksj-db/db mice (male, age 5 weeks) and KKAy mice (female, age 4 weeks) were purchased from Clea Japan, and used in the test after acclimating to the test environment for 1 week. The mice were housed 5 animals to a cage and given unrestricted access to feed (F2, Funabashi Farm) and water.

(ii) Schedule

The body weights of the animals were measured and blood samples were collected on the day the test started, and the animals were divided into two groups of 5 animals per cage based on their body weights and blood glucose levels. Blood samples were collected at the start of the test and days 4, 7 and 14 after the start of the test in the case of the C57BL/ksj-db/db mice, and at the start of the test and on days 4, 7, 14 and 28 after the start of the test in the case of the KKAy mice. Blood samples were collected from the tail vein in an amount equal to one heparinized capillary tube.

(iii) Administration Method

Pravastatin powder was added to the F2 powder to 0.03% and 0.06% (wt/wt), uniformly mixed and provided to the animals in individual cages. The amount of feed and general behaviour were checked at least once a day.

(iv) Measurement

Blood glucose levels were measured on the days when blood samples were collected. The Glucose CII-Test Wako (Wako) was used for measurement of blood glucose levels.

(2) Insulin Tolerance Test Using Pravastatin-Dosed Mice

A group administered with pravastatin by mixing in feed for 2 weeks and a non-dosed group of C57BL/ksj-db/db mice (n=5) were fasted for 2 hours. After measuring the body weight of each animal, insulin (Humalin, Lilly) was administered intraperitoneally at 1 u/kg, and blood samples were collected from the tail vein immediately before the start of administration and at 30, 60, 90 and 120 minutes after the start of administration followed by measurement of blood glucose levels.

(3) Glucose Tolerance Test Using Pravastatin-Dosed Mice

A group administered with pravastatin by mixing in feed for 2 weeks and a non-dosed group of C57BL/ksj-db/db mice (n=5) were fasted for 16 hours starting on the day before the start of the test. After measuring the body weight of each animal, glucose solution (0.5 g/l) was administered intraperitoneally to 2 g/kg, and blood samples were collected from the tail vein immediately before the start of administration and at 30, 60, 90 and 120 minutes after the start of administration followed by measurement of blood glucose levels.

(4) Glucose Uptake Test Using Isolated Adipocytes from Pravastatin-Dosed Mice
(i) Epididymal adipose tissue was excised from a group administered with pravastatin for 1 week and a non-dosed group of C57BL/ksj-db/db mice (n=5). The excised adipose tissue was handled under conditions of 37° C. at all times. The adipose tissue was cut into small pieces with a scissors, followed by the addition of medium (DMEM, 1 mM sodium pyruvate, 25 mM HEPES pH 7.4, 0.1% BSA, 100 u/ml penicillin, 0.1 mg/ml streptomycin) containing 1 mg/ml of collagenase I (Worshington), and shaking at 37° C. and 80 rpm. Following the reaction, 2.5 volumes of the aforementioned medium were added, the adipocytes were screened out by passing the cell suspension through a 260 μm mesh sieve, and again passed through a 100 μm mesh sieve to prepare an adipocyte suspension.

An adipocyte suspension was prepared for C57BL/6J mice (normal mice) in the same manner as described above.
(ii) The glucose uptake test was carried out in the manner as described below. 100 μl of the aforementioned cell suspension, 90 μl of medium and 10 μl of insulin solution were added to a polystyrene tube, while stirring gently to uniformly distribute the adipocytes in each tube, and the adipocytes cultured for 30 minutes at 30° C. Subsequently, 0.6 μCi of $^3$H-labeled 2-deoxyglucose was added and allowed to react for 30 minutes. Following the reaction, the cell suspension was immediately transferred to a centrifuge tube containing silicone oil and centrifuged. After cutting out the oil layer of the upper layer containing adipocytes with a knife, it was transferred to a glass vial containing 4 ml of Hionic Fluor (Perkin-Elmer) liquid scintillation counter cocktail followed by measurement of specific radioactivity. The amount of measured radioactivity of the $^3$H-2-deoxyglucose was used as an indicator of the amount of glucose taken up by the cells.

(5) Results

In (1) above, as a result of administering pravastatin to C57BL/ksj-db/db mice and KKAy mice serving as a model of obesity type 2 diabetes prior to the onset of diabetes, prominent inhibitory action on increases in blood glucose levels was observed (C57BL/ksj-db/db mice: non-dose group 633 mg/dl, dose group 438 mg/dl; KKAy mice: non-dose group 521 mg/dl, dose group 351 mg/dl).

In the insulin tolerance test of (2) above, the pravastatin dose group demonstrated significantly lower blood glucose levels than the non-dose group at 60 minutes after administration of insulin (non-dose group: 411 mg/dl, dose group: 324 mg/dl).

In the glucose tolerance test of (3) above, the pravastatin dose group demonstrated significantly lower blood glucose levels than the non-dose group at 60 minutes after administration of insulin (non-dose group: 517 mg/dl, dose group: 342 mg/dl).

In the C57BL/6J mouse and C57BL/ksj-db/db mouse adipocytes in (4) above, the pravastatin dose group demonstrated increased insulin sensitivity and increased glucose uptake more than the non-dose group. In the C57BL/6J mice, the amount of glucose uptake by the dose group was 1.4 times greater than that by the non-dose group, and in the C57BL/ksj-db/db mice, the amount of glucose uptake by the dose group was 2.0 times greater than that by the non-dose group.

From the aforementioned results, an HMG-CoA reductase inhibitor serving as an active ingredient of the present invention was determined to have superior action of enhancing glucose uptake into warm-blooded animal cells, and be useful as a pharmaceutical composition for enhancement of glucose uptake into warm-blooded animal cells; enhancement of glucose uptake into warm-blooded animal cells in the presence of insulin; treatment of diabetes, hyperglycemia, glucose intolerance or gestational diabetes mellitus; treatment or prevention of diabetes complications (including retinopathy, nephropathy, neuropathy, cataract and coronary artery disease); or, treatment or prevention of diabetes, hyperglycemia, glucose intolerance, gestational diabetes mellitus or diabetes complications (including retinopathy, nephropathy, neuropathy, cataract and coronary artery disease) caused by insulin resistance syndrome.

Formulation Example 1

Tablets

After mixing 10 parts of pravastatin sodium, 71.55 parts of lactose, 20 parts of low substituted hydroxypropyl cellulose (LH21, Shin-Etsu Chemical), 20 parts of crystalline cellulose (Avicel PH101, Asahi Kasei) and 6.5 parts of magnesium metasilicate aluminate (Neusilin FL2, Fuji Chemical Industry) with a Henschel mixer (Mitsui Mining), 13 parts of a 10% aqueous solution of hydroxypropyl cellulose (Nippon Soda) and a suitable amount of water were added to the resulting mixture followed by kneading with a Henschel mixer. The resulting kneaded product was dried for 1 hour at 60° C. with an air dryer. The resulting dried product was sized with a power mill (Dalton) equipped with a 1 mmφ diameter screen, and 129.65 parts of the resulting granules and 0.65 parts of magnesium stearate (NOF Corporation) were mixed with a V-mixer (Tokuju Seisakusho). The resulting mixture was formed into tablets to produce tablets having a diameter of 7.0 mm.

The invention claimed is:

1. A method for enhancing glucose uptake into warm-blooded animal adipocytes, comprising administering to a warm-blooded animal in need thereof an effective amount of pravastatin or pharmacologically acceptable salts or esters thereof sufficient to enhance glucose uptake into warm-blooded animal adipocytes, wherein the glucose uptake occurs from the interstitial fluid of peripheral adipose tissues.

2. A method according to claim 1, wherein the warm-blooded animal is a human.

3. A method according to claim 1, wherein administering an effective amount of pravastatin or pharmacologically acceptable salts or esters thereof comprises administering pravastatin or pharmacologically acceptable salts or esters thereof in the presence of insulin.

4. A method according to claim 1, further comprising administering an effective amount of a second HMG-CoA reductase inhibitor selected from the group consisting of lovastatin, simvastatin, fluvastatin, cerivastatin, atorvastatin, pitavastatin, and rosuvastatin.

5. A method for enhancing insulin-induced glucose uptake into warm-blooded animal adipocytes in an insulin-dependent manner, comprising administering to a warm-blooded animal in need thereof an effective amount of insulin and pravastatin or pharmacologically acceptable salts or esters thereof sufficient to enhance glucose uptake into warm-blooded animal adipocytes, wherein the glucose uptake occurs from the interstitial fluid of peripheral adipose tissues.

6. A method according to claim 5, wherein the warm-blooded animal is a human.

7. A method according to claim 5, further comprising administering an effective amount of a second HMG-CoA reductase inhibitor selected from the group consisting of lovastatin, simvastatin, fluvastatin, cerivastatin, atorvastatin, pitavastatin, and rosuvastatin.

* * * * *